(12) United States Patent
Papineni et al.

(10) Patent No.: US 8,202,544 B2
(45) Date of Patent: Jun. 19, 2012

(54) HIGH CAPACITY NON-VIRAL VECTORS

(75) Inventors: Rao Papineni, Branford, CT (US); Tao Ji, Hamden, CT (US); William E. McLaughlin, Guilford, CT (US)

(73) Assignee: Carestream Health, Inc., Rochester, NY (US)

( * ) Notice: Subject to any disclaimer, the term of this patent is extended or adjusted under 35 U.S.C. 154(b) by 427 days.

(21) Appl. No.: 12/562,184

(22) Filed: Sep. 18, 2009

(65) Prior Publication Data

US 2010/0113695 A1    May 6, 2010

Related U.S. Application Data

(60) Provisional application No. 61/097,883, filed on Sep. 18, 2008.

(51) Int. Cl.
*C12N 15/87* (2006.01)
*C07H 21/02* (2006.01)
*C07K 2/00* (2006.01)

(52) U.S. Cl. ............... 424/499; 424/423; 424/486

(58) Field of Classification Search ............. 424/499, 424/423, 486
See application file for complete search history.

(56) References Cited

U.S. PATENT DOCUMENTS

| | | | |
|---|---|---|---|
| 7,192,744 B2 | 3/2007 | Weber et al. | |
| 2006/0057211 A1* | 3/2006 | Chorny et al. | ............... 424/486 |
| 2007/0264481 A1* | 11/2007 | DeSimone et al. | ........... 428/220 |
| 2008/0181965 A1 | 7/2008 | Leon et al. | |
| 2008/0213377 A1 | 9/2008 | Bhatia et al. | |
| 2009/0196831 A1 | 8/2009 | Yang et al. | |

* cited by examiner

*Primary Examiner* — Kelechi Egwim

(57) ABSTRACT

Non-viral vectors for delivering agents to a site within the body of an animal comprise a biocompatible nanoparticle conjugated to an avidin/biotin complex and a water soluble linear polymer comprising multiple binding sites. The agents to be delivered are conjugated to each of the multiple binding sites, thereby increasing the loading capacity of the system. Where the agents comprise siRNA, each biotin/avidin complex may carry greater than four siRNA. The biocompatible nanoparticle may also comprise a fluorescent dye for in vivo imaging.

9 Claims, 2 Drawing Sheets

HIGH CAPACITY NON-VIRAL VECTORS

CROSS-REFERENCE TO RELATED APPLICATION

This application claims priority to U.S. Provisional App. Ser. No. 61/097,883, filed on 18 Sep. 2008 titled NEUTRAVIDIN AS A HIGH-VOLUME COUPLER, MULTIMODAL IMAGING AGENT AND DRUG DELIVERY to Papineni, the contents of which are incorporated by reference in their entirety.

FIELD OF THE INVENTION

This invention relates generally to non-viral vectors and more particularly to non-viral vectors for delivering agents to a site within a body of an animal, including a human.

BACKGROUND OF THE INVENTION

In vivo delivery vectors are useful for delivering agents to tissues, cells and subcellular locations. The vectors are typically a solid platform upon which a number of substances, such as agents or targeting moieties, may be attached. A number of vectors have been described as suitable for delivering agents as treatments and/or labels to specific tissue, cell or subcellular locations within a body. Such vectors include viruses and the non-viral vectors such as nanoparticles.

Combining non-viral vectors with cell targeting moieties allows non-viral vectors to deliver agents to specific targets. In addition, combining the non-viral vector with a cell penetrating biologic helps ensure that once the vector reaches the target, the agent can be delivered to the inside of, for example, a cell.

The amount of agent that can be delivered per vector depends on several factors including size of the vector to the extent that size increases the amount of surface area available for binding the agent. There is, however, a trade-off between size and ability of the vector and therefore the agent, to be delivered to the target. Through the use of avidin/biotin technology, the amount of agent delivered per vector can be amplified.

A number of substances, such as drugs, peptides, proteins, nucleic acids and carbohydrates can be conjugated with biotin. An avidin molecule binds up to four biotin molecules and thus binds up to four biotinylated agents. Conjugating an avidin molecule to the vector increases the effective surface binding area four-fold.

The ability to deliver the greatest amount of agent with the least amount of carrier is advantageous. For example, some agents, such as ribonucleic acid (RNA) will suffer degradation en route to the target. Thus, in order to help ensure delivery of sufficient amounts of agent to a target site, an increased load to counteract the degradation is advisable. In another example, the targeted area might be small. Increasing the amount of label to the target area increases the ability to visualize the site. Delivering the greatest amount of agent per vector allows for delivery of the greatest amount of the agent.

While the prior art discloses methods for delivering agents to tissues, cells, and/or subcellular locations, it would be beneficial to have a delivery system that would provide high loading capacity of beneficial agents.

SUMMARY OF THE INVENTION

Non-viral vectors of the present invention provide enhanced loading capacity through the incorporation of water soluble linear polymers comprising primary amine groups.

In one embodiment, the non-viral vectors of the presently claimed invention comprise a biocompatible nanoparticle, an avidin protein conjugated to the biocompatible nanoparticle, a biotin molecule conjugated to the avidin protein to form an avidin/biotin complex, a water soluble linear polymer comprising a plurality of primary amine groups and a plurality of agents to be delivered to a site within a body of an animal. The polymer is conjugated to the avidin/biotin complex and comprises multiple binding sites. The plurality of agents are the same or different and are conjugated to the multiple binding sites of the polymer.

In other embodiments, the non-viral vectors include various additional features and components. The plurality of agents may be releasably conjugated to the polymer by a disulfide bond and may include small interfering RNA (siRNA). Each biotin/avidin complex may comprise greater than four agents to be delivered to the site within the body of the animal. The polymer may contain a plurality of primary amine containing functional groups and may be selected from the group consisting of poly (allyl amine), polylysine, chitosan and combinations thereof. The non-viral vector may further include a translocation entity comprising a cell penetrating biologic, a fluorescent agent, a targeting moiety and a plurality of avidin/biotin complexes and a plurality of water soluble linear polymers capable of carrying between about 500 and about 1000 agents to be delivered to the body of the animal.

DETAILED DESCRIPTION OF THE INVENTION

Figure 1:
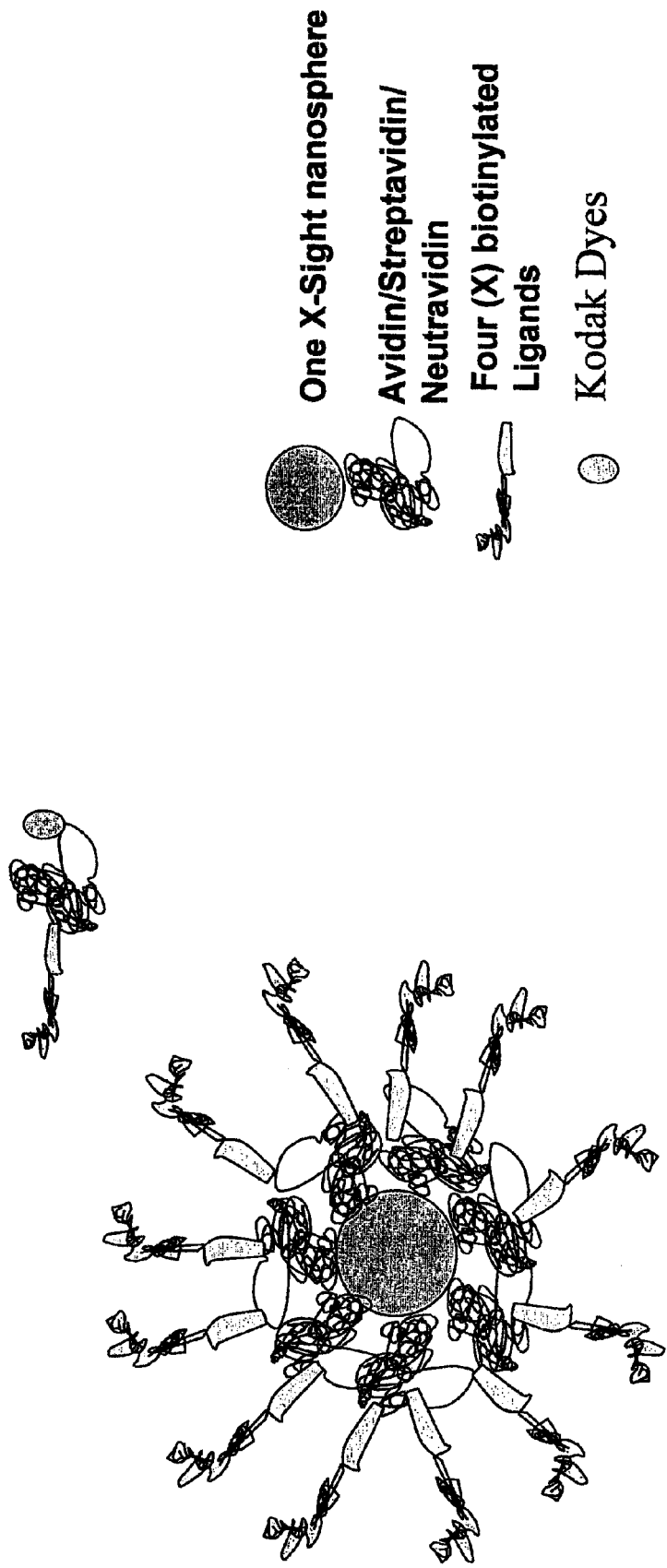
FIG. 1 is an illustration of a non-viral delivery vector, with up to a four-fold amplification of loading capacity.
Figure 2:
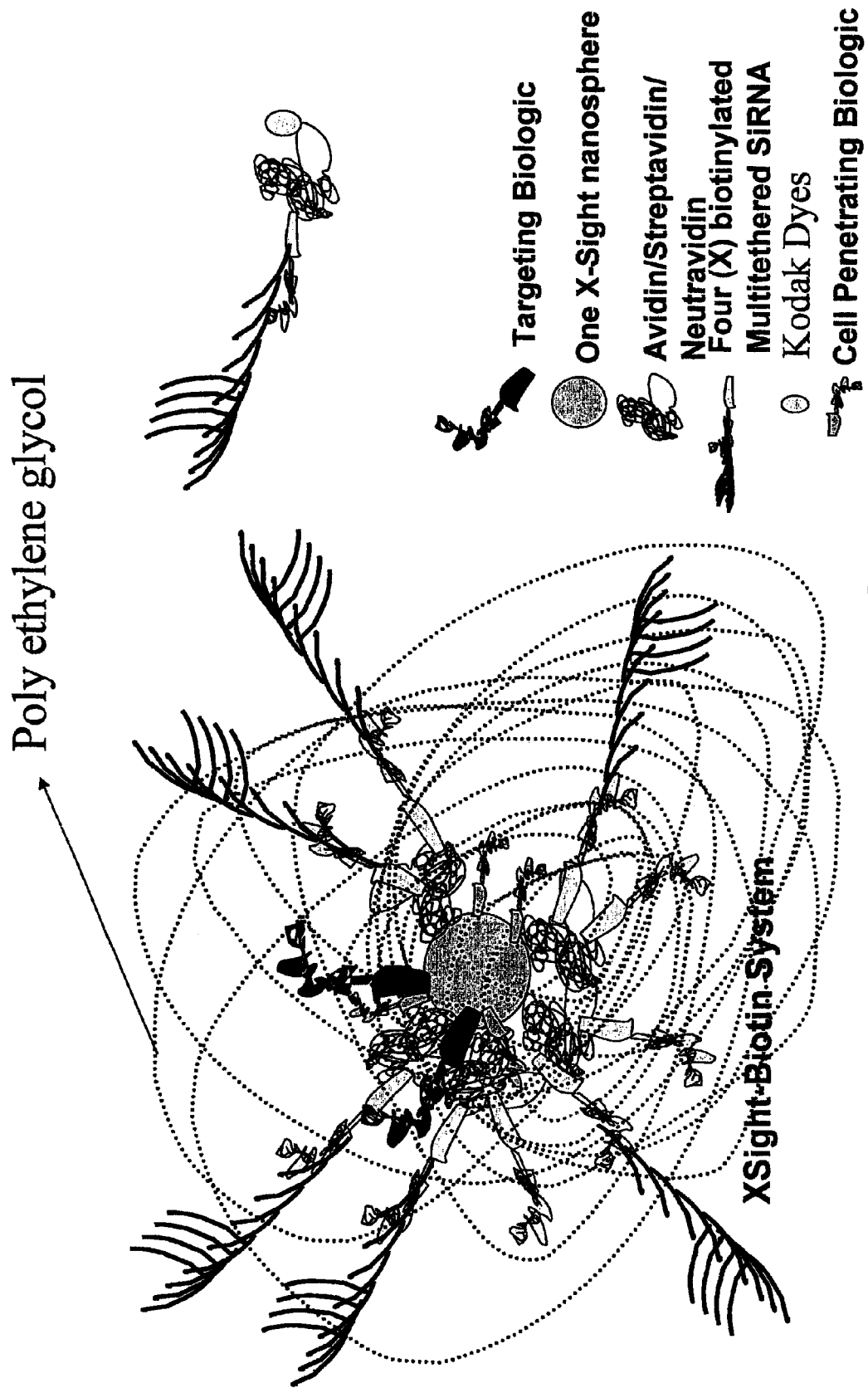
FIG. 2 is an illustration of a non-viral delivery vector with a greater than four-fold amplification of loading capacity.

Reference is made to U.S. Ser. No. 11/732,424, filed 3 Apr. 2007 titled LOADED LATEX OPTICAL MOLECULAR IMAGING PROBES, to Leon et al., incorporated herein by reference.

The non-viral vectors of the present invention deliver an amplified amount of agent to a target tissue, cell or subcellular area, and comprise a solid platform suitable for binding a number of substances. As used herein, the term "agent" means any substance useful in treating and/or diagnosing disease, and/or labeling a target area such that it may be visualized by any suitable mechanism including near infra red, white light and/or X-ray. The non-viral vector may be loaded with multiple units of a single agent or may be loaded with multiple or single units of several different agents.

The non-viral vector further comprises a water soluble linear polymer comprising a plurality of primary amine functional groups that serve as multiple binding sites, wherein said polymer is attached, directly or indirectly to the solid platform. The agent to be delivered may be conjugated to the multiple binding sites. In addition, the non-viral vector may include an avidin-biotin linkage that links the polymer conjugate to the solid platform in a manner that allows for additional amplification of the amount of active agent per non-viral vector. The non-viral vector may additionally comprise a targeting moiety and/or a cell-penetrating moiety.

Nanoparticles are known platforms for use in non-viral vector conjugates. As used herein, the term "nanoparticle" refers to any particle having a diameter of less than 1000 nanometers (nm). Nanoparticles may be biodegradable and made from a number of biocompatible materials such as gelatin, biocompatible polymers or gold. In addition, nanoparticles may be labeled so that they may be detected optically or magnetically thus, biocompatible nanoparticles carrying fluorescent dyes, such as the commercially available Kodak X-Sight Nanospheres are suitable for use with the invention. Due to their surface area and ability to be conjugated with a variety of molecules, nanoparticles provide a solid platform upon which the non-viral vector may be built. As used herein, the term "biocompatible" refers to substances that do not alter the biological functions of a viable organ system, tissue, cell or subcellular area.

The non-viral vector of the invention also comprises a water soluble linear polymer comprising a plurality of primary amine groups conjugated to the nanoparticle, either directly or indirectly. The primary amine groups provide multiple binding sites for the active agent, increasing agent load to amounts greater than that of the nanoparticle alone. Thus any water soluble linear polymer with primary amine groups as multiple binding sites is contemplated as useful in the invention. Examples of useful polymers include poly (allyl amine), polylysine, chitosan. In addition, the invention contemplates conjugating multiple polymers to the nanoparticle. These polymers may also include disulfide bonds with the agent to be delivered such that the agent is releasable after delivery to a target cell through an endogenous cleaving mechanism.

Delivering agents via the non-viral vector system of the invention allows for the amplification of the amount of agent delivered by ~1000-fold over traditional avidin/biotin based delivery systems. For example, the non-viral vector can carry between about 500 and about 1000 individual agents decorated on the surface of the polymers. The advantage of delivering more agent(s) per vector allows for the amplification of a signal or the delivery of more therapeutic units to the target.

The agent to be delivered includes a wide variety of substances that may provide treatment, prophylaxis, diagnostic capabilities and/or provide for visualization of an in vivo target. Suitable agents include small molecules, organometallic compounds, nucleic acids, proteins, peptides, lipids, carbohydrates, radioactive elements and compounds, hormones, drugs, vaccines, immunological agents, and/or combinations thereof. An agent suitable for use in the invention is siRNA, which is capable of silencing the expression of specific genes. If desired, the agent may be labeled with, for example, a fluorescent dye, a radioactive isotope or a radiopaque material so that the agent may be visualized by, for example, fluorescent imaging or X-ray.

Amplification may be achieved utilizing an avidin-biotin technology. Avidin is a tetrameric protein containing four subunits, each of which can bind to biotin. In addition to the protein avidin, at least two avidin derivatives, streptavidin and neutravidin, are capable of binding up to four biotins. As used herein, the term "avidin protein" refers to avidin and any avidin derivative capable of binding to biotin, including avidin, streptavidin and neutravidin.

Biotin, also known as vitamin B7, binds to avidin with well known specificity and affinity. Four biotin molecules may bind with each avidin molecule. A number of substances may be conjugated to biotin. The process of conjugating biotin to a substance is often referred to as biotinylation. For example, drugs, RNA, DNA, amino acids, peptide and proteins may be biotinylated. In addition, polymers may be biotinylated. Once a substance is biotinylated, the substance may be attached to the avidin molecule through the biotin link. Biotin molecules bind equally well to avidin, streptavidin and neutravidin, and any of the avidin derivatives may be used in the avidin-biotin system.

The benefit of using avidin-biotin technology is that the delivered amount of a biotinylated agent can be amplified four-fold due to the ability to attach four biotinylated molecules to each avidin molecule. Where the biotinylated molecule is a polymer and the agent is attached to the multiple binding sites of the polymer, the amplification of agent loading is increased greater than four-fold, thus providing more agent per delivery vector, which in turn provides the greatest amount of active to the target.

In addition to a platform, polymer and agent, the non-viral vector of the invention may include a modulating entity. The modulating entity may be any entity that alters or affects the efficiency, specificity, and/or accuracy of delivery of the non-viral vector and/or agent. Thus, the modulating agent may provide protection for the agent and/or control delivery and/or activity of the agent and/or nanoparticle. The modulating entity may be physically associated with any part of the non-viral vector, including the nanoparticle or the agent. The modulating entity may include a translocation entity, a targeting entity and/or protective entity, further described below.

A translocation entity is capable of inducing or enhancing the translocation of the non-viral vector into a cell or into a subcellular area. As used herein, the term "translocation entity" refers to any entity capable of inducing or enhancing delivery of the agent to the target. Translocation entities suitable for use in the invention include peptides, proteins, glycoproteins, nucleic acids, carbohydrates, lipids and small molecules. A particularly useful translocation entity is a cell penetrating biologic such as penetratin, transportan, and myristoylated polyarginine peptides.

A targeting entity may provide enhanced accuracy in delivering the non-viral vector to the desired target. As used herein, a "targeting entity" is any entity that binds to a component associated with an organ, tissue, cell, subcellular area and/or extracellular matrix. Examples of targeting entities include nucleic acids, amino acids, peptides, proteins, glycoproteins, lipids, carbohydrates, aptamers, phage particles, monoclonal antibodies specific to cell types, small molecules, antibodies or fragments thereof and antigens or fragments thereof.

Specifically targeting the non-viral vector and hence the agent provides advantages such as reducing side-effects. For example, if it is desirous to silence a gene only in a particular subset of cells, by specifically targeting that subset of cells, the non-targeted cells will not be impacted by the gene silencing agent.

A protective entity may provide protection to the non-viral vector and/or the agent to be delivered by the non-viral vector, during transit to the target. The nature of the protective entity depends on the non-viral vector and/or agent to be protected. The protective entity may be associated with the agent itself or with the non-viral vector. The protective entity may be in the form of a protective layer or coating. Protective entities include PEG or a PEG derivative, phospholipid-(PEG), proteins (e.g., bovine serum albumin), silica, lipids, and carbohydrates (e.g., dextran). A particularly useful protective entity is PEG, which is suitable for protecting RNA from the extracellular enzymes that are present during transit.

As described, a non-viral vector comprises a number of components. The components may be associated with each other, directly or indirectly, in a variety of ways. A stepwise process is used to prepare the non-viral vectors of the present invention. First, a biocompatible nanoparticle, such as the commercially available Kodak X-Sight Nanospheres is modified with N-[β-Maleimidopropyloxy]succinimide ester (BMPS). Next, a neutravidin protein containing thiol groups is prepared and conjugated to the nanoparticle. Biotin is then conjugated to the avidin protein and polymers containing multiple binding sites are conjugated to the biotin. Finally, the agents to be delivered to a site within a body of an animal are conjugated to the multiple binding sites of the polymer. A more detailed version of this process appears at Example 1 herein.

If desired, a targeting moiety, such as an antibody, which has been biotinylated, is attached to the nanoparticle and the residual biotin completely removed. The amount of the biotinylated antibody is enough to occupy about one biotin site stoichiometrically (1:1 Targeting moiety and non-viral delivery vector). Attachment of the biotinylated antibody typically involves a 45 minute incubation on ice, with repeated tapping every 5-10 minutes. In a similar manner, and if desired, a cell penetrating moiety may also be attached, provided that the cell penetrating moiety is present in an amount such that it occupies only about 2-3 biotin binding sites. The final step is to add the polymer-siRNA conjugate at a ratio sufficient to occupy 10-12 sites of biotin binding sites. Again a 45 minute incubation period, on ice, with repeated tapping every 5-10 minutes occurs.

The non-viral vector of the invention is useful for the in vivo delivery of high volumes of treating, prophylaxis and/or labeling agents. Further, the non-viral delivery vector of the invention can be configured such that the delivery is specifically directed to particular targeted areas within the body. High volumes of agents are often important when, for example the target is small and an amplified signal is required for visualization or where the agent itself is subject to degradation. The ability to initially start with a high volume of agent may counterbalance the degradation such that when the agent is delivered to the target, it is delivered in an effective quantity.

Non-viral vectors of the invention are intended for use in any living entity such as cells, tissue and organs. Preferably, the living entity is an intact animal. As used herein, the term "animal" includes mammals, reptiles, amphibians, birds, fish and insects.

Non-viral vectors may be introduced into the body of an intact animal by any suitable means. For example, the non-viral vector may be introduced into the body as a pharmaceutical composition. Formulation of pharmaceutical compositions may be by any acceptable pharmacological method including combining the non-viral vector with an excipient and/or one or more additional accessory ingredients, and if necessary, shaping the composition into the desired dosage forms.

Relative amounts of the non-viral vector, which includes the agent, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. For example, the composition may comprise between 0.1% and 100% (w/w) of the non-viral vector. Pharmaceutical compositions may be introduced by any suitable means including oral, parental or intravenous.

Once administered, if desired, the delivery of the agent to the target may be monitored. For example, where a nanoparticle labeled with a fluorescent dye is utilized in the invention, delivery may be monitored by microscopic imaging. In another example, where the agent is a label or is labeled with a fluorescent dye or a radiopaque materials, delivery may be monitored by microscopy or X-ray, respectively. Methods for imaging specific areas within the body are well-known to those of skill in the art.

The following experimental examples are included to further illustrate embodiments of the invention. These examples are not intended to limit the invention in any manner.

EXAMPLE 1

Preparation of the Non-Viral Vector Delivery System (Prophetic)

Modification of Nanoparticles with BMPS. Kodak X-Sight Nanospheres (40 μL, 80 μM) are added to 60 μL of phosphate buffered saline (PBS) (0.1 M, 0.15 M NaCl, pH 7.5) and then added with 10.7 μL, of 30 mM×BMPS dissolved in anhydrous Dimethyl sulfoxide (DMSO). The mixture is stirred at room temperature for 1 h. The maleimide-modified nanoparticles are purified on an illustra NAP-5 column eluted with PBS (0.1 M, 0.15 M NaCl, pH 7.2)/10 mM Ethylenediaminetetraacetic acid disodium salt (EDTA).

Preparation of Neutravidin Having Thiol Groups. Neutravidin (1 mg) is dissolved in 1 ml of PBS (0.1 M, 0.15 M NaCl, pH 7.2)/10 mM EDTA. 25 μL of 20 mM N-Succionimidyl-3-(2-PyridlDithio)-Propionate (SPDP) dissolved in DMSO is added to the neutravidin solution. The mixture is incubated at room temperature for 1 h and then added with 10 μL of 1 M dithiothreitol (DTT) dissolved in PBS (0.1 M, 0.15 M NaCl, pH 7.2)/10 mM EDTA. The mixture is incubated at room temperature for 30 min and purified on a Sephadex G-25 column equilibrated with PBS (0.1 M, 0.15 M NaCl, pH 7.2)/10 mM EDTA).

Conjugation of Neutravidin to Nanoparticles. Maleimide—modified nanoparticles and Neutravidin having thiol groups are mixed together and incubated at RT for 2 h at RT. The mixture is concentrated to ~100 μL and fractionated on a Superdex 200 column eluted with 1×PBS (10 mM sodium phosphate, 0.15 M NaCl, pH 7.2). The concentration of the purified nanoparticle—neutravidin conjugates is determined by UV absorbance at λmax.

Attachment of Biotin and SPDP to Polymers. Polymer (Mw ~100000, 75 nmol) is dissolved in 2 mL of PBS (0.1 M, 0.15 M NaCl, pH 7.2) and then added with 7.5 μL of 100 mM NHS-Biotin dissolved in DMSO. The mixture is stirred at room temperature for 30 min and then added with 37.5 μL of 100 mM SPDP dissolved in DMSO. The mixture is incubated for 1 h at room temperature. Then the mixture is concentrated and purified on a Sephadex G-25 column eluted with PBS (0.1 M, 0.15 M NaCl, pH 7.2)/10 mM EDTA.

Attachment of siRNA to polymers. The above purified polymers containing biotin and SPDP is mixed with siRNA in PBS/10 mM EDTA in a 1:10 molar ratio. The mixture is stirred at room temperature for 2 h and purified on a Sephadex G-50 column eluted with 1×PBS (10 mM sodium phosphate, 0.15 M NaCl, pH 7.2).

EXAMPLE 2

Use of Non-Viral Vector Delivery System (Prophetic)

Tumor cells are grown orthotopically in nude mice. The mice are then injected, intravenously, with the final product described in Example 1. Trafficking can be monitored by X-Ray and near infra red imaging (NIRF) using the Kodak In Vivo Multispectral Imaging System FX. Combining both methods of imaging will allow for confirmation that the non-viral vector delivery system, including the siRNA, has reached its target location.

While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation. The actual scope of the invention is intended to be defined in the following claims.

What is claimed is:

1. A non-viral vector comprising:
a biocompatible nanoparticle;
an avidin protein conjugated to the biocompatible nanoparticle;
a biotin molecule conjugated to the avidin protein to form an avidin/biotin complex;
a water soluble linear polymer conjugated to the avidin/biotin complex, said water soluble linear polymer comprising a plurality of primary amine functional groups that serve as multiple binding sites; and
a plurality of agents to be delivered to a site within a body of an animal, wherein said plurality of agents are the same or different and are conjugated to the multiple binding sites.

2. The non-viral vector of claim 1, wherein the plurality of agents are releasably conjugated to the multiple binding sites by a disulfide bond.

3. The non-viral vector of claim 1, wherein each biotin/avidin complex comprises greater than four agents to be delivered to the site within the body of the animal.

4. The non-viral vector of claim 1, further comprising a translocation entity comprising a cell penetrating biologic.

5. The non-viral vector of claim 1, wherein the plurality of agents to be delivered comprise siRNA.

6. The non-viral vector of claim 1, wherein the biocompatible nanoparticle comprises a fluorescent agent.

7. The non-viral vector of claim 1, wherein the water soluble linear polymers are selected from the groups consisting of poly (allyl amine), polylysine, chitosan and combinations thereof.

8. The non-viral vector of claim 1, wherein the non-viral vector comprises a plurality of avidin/biotin complexes and a plurality of water soluble linear polymers capable of carrying between about 500 and about 1000 agents to be delivered to the body of the animal.

9. The non-viral vector of claim 1, further comprising a cell targeting moiety conjugated to the biotin molecule.

* * * * *